United States Patent [19]

Paatz et al.

[11] Patent Number: 5,719,115
[45] Date of Patent: Feb. 17, 1998

[54] COATED ENZYME PREPARATION FOR DETERGENTS AND CLEANING FORMULATIONS

[75] Inventors: Kathleen Paatz; Wilfried Raehse, both of Duesseldorf, Germany; Werner Pichler, Kundl, Austria; Norbert Kuehne, Haan; Horst Upadek, Ratingen, both of Germany

[73] Assignee: Henkel Kommanditgesellschaft auf Aktien, Duesseldorf, Germany

[21] Appl. No.: 578,526

[22] PCT Filed: Jun. 27, 1994

[86] PCT No.: PCT/EP94/02079

§ 371 Date: Mar. 5, 1996

§ 102(e) Date: Mar. 5, 1996

[87] PCT Pub. No.: WO95/02031

PCT Pub. Date: Jan. 19, 1995

[30] Foreign Application Priority Data

Jul. 5, 1993 [DE] Germany ............... 43 22 229.3

[51] Int. Cl.$^6$ ............... C11D 3/386; C11D 1/68; C11D 3/40
[52] U.S. Cl. ............... 510/392; 510/530; 510/226; 510/320; 510/474; 435/188
[58] Field of Search ............... 510/392, 530, 510/226, 320, 474; 435/188

[56] References Cited

U.S. PATENT DOCUMENTS

| | | | |
|---|---|---|---|
| 4,661,452 | 4/1987 | Markussen et al. | 435/187 |
| 4,689,297 | 8/1987 | Good et al. | 435/174 |
| 4,867,895 | 9/1989 | Choy | 252/91 |
| 4,973,417 | 11/1990 | Falholt et al. | 252/95 |
| 5,093,021 | 3/1992 | Coyne et al. | 252/91 |
| 5,254,283 | 10/1993 | Arnold et al. | 252/174.12 |
| 5,258,132 | 11/1993 | Kamel et al. | 252/94 |
| 5,318,714 | 6/1994 | Markussen et al. | 252/95 |
| 5,324,469 | 6/1994 | Arnold | 435/187 |

FOREIGN PATENT DOCUMENTS

| | | |
|---|---|---|
| 0206418 | 12/1986 | European Pat. Off. . |
| 9211347 | 7/1992 | WIPO . |
| 9307260 | 4/1993 | WIPO . |

Primary Examiner—Paul Lieberman
Assistant Examiner—Kery A. Fries
Attorney, Agent, or Firm—Ernest G. Szoke; Wayne C. Jaeschke; Real J. Grandmaison

[57] ABSTRACT

Enzyme granules containing an enzyme, an inorganic or organic carrier material and a uniform outer pigment-containing coating layer on the granules, wherein the outer coating layer contains 30 to 50% by weight of fine-particle inorganic pigment, 45 to 60% by weight of an alcohol or alcohol mixture having a melting point of from 45° C. to 65° C., up to 15% by weight of an emulsifier for the alcohol or alcohol mixture, up to 5% by weight of a dispersant for the pigment and up to 3% by weight of water, based on the weight of the outer coating layer.

15 Claims, No Drawings

COATED ENZYME PREPARATION FOR DETERGENTS AND CLEANING FORMULATIONS

BACKGROUND OF THE INVENTION

1. Field of the Invention

This invention relates to enzyme granules, to a process for their production and to their use in solid detergents and cleaning formulations.

2. Discussion of Related Art

Enzymes, especially proteases, are widely used in detergents, washing aids and cleaning products. Normally, the enzymes are not used as concentrates, but rather in the form of mixtures with a diluent/carrier material. If enzyme preparations of this type are added to conventional detergents, a considerable reduction in enzyme activity can occur during storage, especially if bleaching-active compounds are present. Application of the enzymes to carrier salts and simultaneous granulation in accordance with DE-OS 16 17 190 or by adhesion using nonionic surfactants in accordance with DE-OS 16 17 118 or aqueous solutions of cellulose ethers in accordance with DE-OS 17 87 568 does not lead to a significant improvement in storage stability because the sensitive enzymes are generally situated on the surface of the carrier in mixtures of the type in question. Although the stability of the enzymes in storage can be significantly increased by coating the enzymes with or encapsulating them in the carrier material and converting them into the required particle form by extrusion, pressing and marumerizing, as described for example in DE-PS 16 17 232, in DE-OS 20 32 768 and in DE-ASS 21 37 042 and 21 37 043, corresponding enzyme preparations have poor solubility properties. The undissolved particles can become caught up in and thus soil the washing or pass into the wastewater without being used. Although the encapsulating compositions known from DE-OS 18 03 099, which consist of a mixture of solid acids or acidic salts and carbonates or bicarbonates and which disintegrate on addition of water, improve the solubility of the enzyme preparations, they are extremely sensitive to moisture and, accordingly, require additional protective measures.

EP 168 526 describes enzyme granules which contain water-swellable starch, zeolite and a water-soluble granulation aid. This document proposes a production process for such formulations which essentially comprises concentrating a fermenter solution freed from insoluble constituents, introducing the additives mentioned, granulating the resulting mixture and optionally coating the granules with film-forming polymers and dyes. The process using the additive mixture proposed therein is advantageously carried out with fermentation solutions which have been concentrated to a relatively high dry matter content, for example of 55% by weight. In addition, the granules thus produced have such a high dissolving or disintegration rate under washing conditions that some of them even disintegrate relatively quickly during storage and the enzymes are deactivated.

International patent application WO 92/11347 describes enzyme granules for use in granular detergents and cleaning compositions which contain 2% by weight to 20% by weight of enzyme, 10% by weight to 50% by weight of swellable starch, 5% by weight to 50% by weight of water-soluble organic polymer as granulation aid, 10% by weight to 35% by weight of cereal flour and 3% by weight to 12% by weight of water. These additives enable the enzyme to be processed without significant losses of activity.

International patent application WO 93/07263 describes enzyme-containing granules consisting of a water-soluble or water-dispersible core coated with a vinyl polymer to which a layer of enzyme and vinyl polymer is applied, the granules being externally coated with vinyl polymer. The outer coating may also contain pigments. Unfortunately, the multilayer structure of these enzyme granules makes them relatively difficult to produce.

International patent application WO 93/07260 describes various coating materials for dust-free enzyme granules which are produced by spraying of a fermentation broth onto a hydratable carrier material. Fatty acid esters, alkoxylated alcohols, polyvinyl alcohol, polyethylene glycol, sugar and starch inter alia are mentioned as suitable. There is no reference whatever to the coating system which has now been found to be particularly suitable and simple to process.

The coating compositions used in the cited documents for the outermost coating layer are normally applied to the enzyme granules in the form of an aqueous dispersion in a fluidized bed dryer. The surface of the granules at least is in danger of being destroyed through dust abrasion in the fluidized bed, leading to an increased percentage of extremely fine-particle material in the enzyme granules which cannot be used for incorporation in conventional particulate detergents or cleaning products because it is not uniformly distributed in the mixture formed. Accordingly, every effort is made to keep the percentage of fines in the enzyme granules as small as possible to ensure that as little as possible has to be removed by sieving or air separation.

Accordingly, the problem addressed by the present invention was to provide a coating system which, when uniformly applied to enzyme-containing granules, would counteract surface destruction of the granules, would increase the stability of the enzyme in storage by forming a protective coating around the granules as a whole, would enable any intrinsic color of the uncoated enzyme granules to be masked and would eliminate any troublesome odor of the uncoated granules, probably by preventing diffusion of the substances responsible to the surface of the enzyme granules.

DESCRIPTION OF THE INVENTION

The present invention relates to enzyme granules suitable for incorporation in detergents or cleaning compositions, more particularly particulate detergents or cleaning compositions, containing enzyme and inorganic and/or organic carrier material and a uniform outer pigment-containing coating layer, characterized in that the outer coating layer consists of a coating system containing 30 to 50% by weight of fine-particle inorganic pigment, 45 to 60% by weight of an alcohol solid at room temperature with a melting point in the range from 45° C. to 65° C., up to 15% by weight and, more particularly, from 5% by weight to 15% by weight of an emulsifier for the alcohol, up to 5% by weight and, more particularly, from 0.2% by weight to 3% by weight of dispersant for the pigment and up to 3% by weight of water.

The present invention also relates to a process for the production of enzyme granules with an average particle size of 0.8 mm to 1.2 mm suitable for incorporation in particulate detergents or cleaning compositions by extruding an enzyme compound formed by mixing of a concentrated fermentation broth optionally freed from insoluble constituents beforehand by microfiltration with inorganic and/or organic carrier material as additive, optionally spheronizing the extrudate in a spheronizer, drying and applying an outer coating layer, an outer coating layer of a coating system of 30% by weight to 50% by weight of fine-particle inorganic pigment, 45% by weight to 60% by weight of alcohol with a melting point of 45° C. to 65° C., up to 15% by weight and, more particularly, 5% by weight to 15% by weight of emulsifier for the alcohol and up to 5% by weight and, more particularly, 0.2% by weight to 3% by weight of dispersant for the pigment being applied in a fluidized bed of extrudate.

The alcohol component of the coating system is preferably a primary linear alcohol containing 14 to 22 carbon atoms or a mixture thereof. The alcohols mentioned include, in particular, myristyl alcohol, cetyl alcohol, stearyl alcohol, arachidyl alcohol, behenyl alcohol and mono- to tri-unsaturated alcohols of corresponding chain length, the above-mentioned alcohol component of the coating system having to have a melting point of 45° C. to 65° C. and, more particularly, in the range from 50° C. to 60° C., the term melting point in this context being understood to be the temperature at which 100% of the alcohol component is present in liquid form on heating. Where alcohol mixtures are used, mixtures containing small amounts, normally below 15% by weight, based on the alcohol mixture, of components liquid at room temperature may also be used providing the alcohol mixture as a whole appears solid at room temperature and has a solidification point in the range from 45° C. to 65° C. and more particularly in the range from 50° C. to 60° C. The solidification point is the temperature at which material heated to a temperature above the melting point solidifies on cooling. It can be determined with a rotating thermometer by the method according to DIN ISO 2207.

Suitable emulsifiers for the alcohol component are substances which are capable of emulsifying the alcohol component in water so that a mixture sprayable at temperatures of up to 95° C. is formed and/or which enable the coating system to be converted into a uniform melt sprayable at temperatures of up to 120° C. A criterion in this regard is that liquids with viscosities of up to about 10,000 cPs can generally be sprayed without difficulty by means of suitable equipment at the temperatures mentioned and applied to enzyme granules. Emulsifiers for the alcohol component of the coating system include, for example, the ethoxylation products of the alcohols mentioned, their reaction products with on average 25 to 80 mole equivalents and, more particularly, 30 to 45 mole equivalents of ethylene oxide being preferred. If the coating system is applied to the enzyme granules in the form of an aqueous dispersion, compounds with degrees of ethoxylation of 25 to 50, i.e. reaction products of 25 to 50 mole equivalents of ethylene oxide, are preferred among the compounds mentioned. Alternatively or in addition to the alcohol ethoxylates, ethoxylated fatty acids with a degree of ethoxylation of preferably 3 to 9, ethoxylated fatty acid amides with a degree of ethoxylation of preferably 4 to 11 and/or ethoxylation products of hydroxy fatty acids containing 1 to 6 carbon atoms in the alcohol part of the ester, for example ricinoleic acid glyceride, the degree of ethoxylation preferably being 5 to 80 and, more preferably, 20 to 40, may also be used as the emulsifier component in the coating system. The fatty acid component of the substances mentioned preferably contains 12 to 22 carbon atoms. If desired, the ethoxy groups in the emulsifiers mentioned may be at least partly replaced by propoxy groups.

The inorganic pigments with which any troublesome colors of the enzyme granules can be masked include, for example, calcium carbonate, titanium dioxide, which may be present in the rutile or anatase crystal modification, zinc oxide, zinc sulfide, white lead (basic lead carbonate), barium sulfate, aluminium hydroxide, antimony oxide, lithopone (zinc sulfide/barium sulfate), kaolin, chalk and/or mica. These pigments are present in such fine-particle form that they may be dispersed in a melt of the other components of the coating system or in water. The average particle size of such pigments is normally in the range from 0.004 µm to 50 µm. Particularly in cases where the pigment or rather the coating system as a whole is to be used in the form of an aqueous dispersion, this dispersion preferably contains dispersants for the pigment. Such dispersants may be inorganic, for example aluminium oxide or silicon oxide, which may also serve as pigments, or organic, for example diethylene glycol or dipropylene glycol. Pigments surface-modified with dispersants may also be used. Titanium dioxide pigment, more particulary in the rutile form, surface-modified with Al, Si, Zr or polyol compounds, of the type marketed for example as Kronos® 2132 (Kronos-Titan) or Hombitan® R 522 (Sachtleben Chemie GmbH), is preferably used. The Tiona® RLL, AG and VC types available from Solvay and the Bayertitan® RD, R-KB and AZ types available from Bayer AG may also be used.

Suitable enzymes are, above all, the proteases, lipases, amylases and/or cellulases obtained from microorganisms, such as bacteria or fungi, proteases produced from bacillus species and mixtures thereof with amylases being preferred. They are obtained in known manner by fermentation processes from suitable microorganisms which are described, for example, in DE-OSS 19 40 488, 20 44 161, 22 01 803 and 21 21 397, in U.S. Pat. Nos. 3,632,957 and 4,264,738 and in European patent application EP 006 638. The process according to the invention may be used with particular advantage for the formulation of highly active proteases, which are known for example from International patent application WO 91/2792, because their stable incorporation in detergents often presents problems and because the formation of unwanted enzyme dusts is avoided in accordance with the invention. Enzymes are present in the granules according to the invention in quantities of preferably 4% by weight to 20% by weight. If the enzyme granules according to the invention are a protease-containing formulation, the protease activity is preferably 150,000 protease units (PU, as determined by the method described in Tenside Z (1970), 125) to 350,000 PU and, more particularly, 160,000 PU to 300,000 PU per gram of enzyme granules.

In principle, suitable carrier materials for the enzyme are any organic or inorganic powders which do not destroy or deactivate the enzymes to be granulated at all, or only negligibly, and which are stable under the granulation conditions. Substances such as these include, for example, starch, cereal flour, cellulose powder, alkali metal alumosilicate, more particularly zeolite, layer silicate, for example bentonite or smectite, and water-soluble inorganic or organic salts, for example alkali metal chloride, alkali metal sulfate, alkali metal carbonate or alkali metal acetate, sodium or potassium being the preferred alkali metals. A mixture of carrier materials consisting of water-swellable starch, cereal flour and, optionally cellulose powder and alkali metal carbonate is preferably used.

The water-swellable starch is preferably a corn starch, rice starch, potato starch or a mixture thereof, corn starch being particularly preferred. Swellable starch is present in the enzyme granules according to the invention in quantities of, preferably, 20% by weight to 50% by weight and, more preferably, 25% by weight to 45% by weight. The sum total of the quantities of swellable starch and flour is preferably not more than 80% by weight and, more particularly, from 32% by weight to 65% by weight.

The cereal flour is a product obtainable in particular from wheat, rye, barley or oats or a mixture of such flours, whole-grain flours being preferred. A whole-grain flour is understood to be a flour which has not been fully ground and which has been produced from or consists at least predominantly of whole unshelled grains, the rest consisting of fully ground flour or starch. Commercial wheat flours, such as type 440 or type 550, are preferably used. Ground products of the cereals leading to the swellable starches mentioned above may also be used providing it is ensured that the flours have been produced from whole grains. It is known that the flour component of the additive mixture provides for a significant reduction in the odor of the enzyme preparation which exceeds by far the reduction in odor produced by the incorporation of equal quantities of corresponding starch types. Corresponding cereal flour is present in the enzyme granules according to the invention in quantities of, preferably, 10% by weight to 35% by weight and, more preferably, 15% by weight to 25% by weight.

The enzyme granules according to the invention preferably contain 1% by weight to 50% by weight and preferably 5% by weight to 25% by weight, based on the granules as a whole, of a granulation aid containing alkali metal carboxymethyl cellulose with degrees of substitution of 0.5 to 1 and polyethylene glycol and/or alkyl polyethoxylate as a further component of the carrier material. This granulation aid preferably contains—based on the final enzyme granules—0.5% by weight to 5% by weight of alkali metal carboxymethyl cellulose with degrees of substitution of 0.5 to 1 and up to 3% by weight of polyethylene glycol and/or alkyl polyethoxylate. In a particularly preferred embodiment, at least 0.5% by weight and, more particularly, 0.8% by weight to 2% by weight of polyethylene glycol with an average molecular weight below 1,000 and/or alkyl polyethoxylate containing at least 30 ethoxy groups is present where the granulation aid contains more than 2% by weight of alkali metal carboxymethyl cellulose. Carboxymethyl cellulose with higher degrees of substitution, i.e. with degrees of substitution of up to 3, is preferably not present in the granulation aid.

Other cellulose or starch ethers, such as carboxymethyl starch, methyl cellulose, hydroxyethyl cellulose, hydroxypropyl cellulose and corresponding cellulose mixed ethers, gelatine, casein, tragacanth, maltodextrose, sucrose, invert sugar, glucose sirup or other water-soluble or readily water-dispersible oligomers or polymers of natural or synthetic origin, may optionally be used as additional components of the granulation aid. Useful synthetic water-soluble polymers are polyacrylates, polymethacrylates, copolymers of acrylic acid with maleic acid or compounds containing vinyl groups, also polyvinyl alcohol, partly hydrolyzed polyvinyl acetate and polyvinyl pyrrolidone. If the compounds mentioned above are compounds containing free carboxyl groups, they are normally present in the form of their alkali metal salts, more particularly their sodium salts. These additional granulation aids may be present in the enzyme granules according to the invention in quantities of up to 10% by weight and, more particularly, in quantities of 0.5% by weight to 8% by weight. Although polyethylene glycols of relatively high molecular weight, i.e. those with an average molecular weight above 1,000, may be used as synthetic water-soluble polymers with a dust-binding effect, they do give rise to an unwanted increase in the necessary dissolving time of the granules so that these substances are preferably absent altogether from the enzyme granules according to the invention.

The enzyme granules according to the invention are preferably produced from fermenter broths which are freed from insoluble impurities, for example by microfiltration. The microfiltration is preferably carried out as crossflow microfiltration using porous tubes with micropores larger than 0.1 μm in size, flow rates of the concentrate solution of more than 2 m/s and a pressure difference to the permeate side of less than 5 bar, as described for example in European patent application EP 200 032. The microfiltration permeate is then concentrated, preferably by ultrafiltration optionally followed by vacuum evaporation. The concentration process may be carried out as described in International patent application WO 92/11347 in such a way that only relatively low dry matter contents of, preferably, 5% by weight to 50% by weight and, more preferably, 10% by weight to 40% by weight are obtained. The concentrate is added to a dry, powder-form or granular mixture of the above-described additives best prepared in advance. The water content of the mixture should be selected so that it can be converted during compounding with stirring and beating tools into granular particles non-tacky at room temperature and can be plastically deformed and extruded under relatively high pressures. The free-flowing compound is then processed in basically known manner in a kneader and an adjoining extruder to form a plastic, substantially homogeneous paste which can undergo an increase in temperature to between 40° and 60° C. and, more particularly, to between 45° and 55° C. as a result of compounding. The material leaving the extruder is passed through a multiple bore die followed by a cutting blade so that it is reduced to cylindrical particles of predetermined size. The diameter of the bores in the multiple-bore die is best from 0.7 mm to 1.2 mm and preferably from 0.8 mm to 1.0 mm. The particles present in this form may then be dried and coated with the coating system according to the invention. However, it has been found to be of advantage to spheronize the cylindrical particles leaving the extruder and cutter before they are coated, i.e. to round them off and to "deflash" them in suitable machines. A machine consisting of a cylindrical container with stationary, fixed side walls and a friction plate rotatably mounted on its base is used for this purpose. Machines of this type are marketed under the name of Marumerizer® and are described, for example, in DE-ASS 21 37 042 and 21 37 043. Any fines present with a particle size below 0.1 mm and, more particularly, below 0.4 mm and any coarse particles present with a particle size of more than 2 mm and, more particularly, more than 1.6 mm may then be removed by sieving or air separation and optionally returned to the production process. After spheronizing, the spherical particles are dried continuously or in batches, preferably in a fluidized bed dryer, at feed air temperatures of preferably 35° C. to 50° C. and, more particularly, at a product temperature of not more than 42° C. to the required residual moisture content of, for example, 4% by weight to 10% by weight and, more particularly, 5% by weight to 8% by weight, based on the granules as a whole.

The coating system according to the invention is applied as an outer coating after or preferably during the drying process. In one embodiment of the production process according to the invention, the coating system is introduced into the fluidized bed of extrudate in the form of a dispersion preferably containing 50% by weight to 70% by weight of water and 30% by weight to 50% by weight of the coating system, the coating system containing in particular 1% by weight to 2.5% by weight, based on the coating system as a whole, of dispersant for the pigment. The water introduced through the aqueous dispersion is removed again during the simultaneous drying process or during a subsequent drying process. In another embodiment of the production process according to the invention, the coating system is applied to the extrudate, preferably with cooling, as a heated liquid present at a temperature of 5° C. to 45° C. above the melting point of the alcohol component. In addition, a combination of these procedures in which part of the coating system is applied in the form of an aqueous dispersion and a second part in the form of a melt is possible. 6% by weight to 15% by weight, based on the final granules, of the coating system is preferably applied to the enzyme-containing extrudate as an outer coating layer.

The enzyme preparation obtained by the process according to the invention consists of substantially rounded, uniformly coated and dust-free particles which generally have an apparent density of around 500 to 900 grams per liter and, more particularly, 650 to 880 grams per liter. The granules according to the invention are distinguished by very high stability in storage, more particularly at temperatures above room temperature and high air humidity, and by rapid solubility in the wash liquor. The enzyme granules according to the invention preferably release 100% of their enzyme activity in 3 minutes and, more particularly, in 90 seconds to 2 minutes in water with a temperature of 25° C.

The enzyme granules according to the invention or produced by the process according to the invention are preferably used for the production of solid and, in particular, particulate detergents or cleaning products which can be obtained simply by mixing the enzyme granules with other powder components typically present in detergents or cleaning compositions. For incorporation in particulate detergents, the enzyme granules preferably have particle sizes in the range from 0.8 mm to 1.2 mm. The granules according to the invention preferably contain less than 2% by weight and, more particularly, at most 1.4% by weight of particles with sizes outside the 0.4 mm to 1.6 mm range.

EXAMPLES

Example 1

A harvest pulp obtained after fermentation, as described in International patent application WO 91/2792, with an activity of 75,000 protease units per g (PU/g) was concentrated in an ultrafiltration unit after removal of the fermentation residues by decantation and microfiltration. After further concentration by vacuum evaporation, the aqueous enzyme suspension contained 700,000 PU/g. This protease concentrate was mixed with additives (3.5% by weight of sucrose, 4.5% by weight of cellulose, 3% by weight of carboxymethyl cellulose with a degree of substitution of 0.65 to 0.75, 19% by weight of wheat flour, 35% by weight of corn starch and 3% by weight of polyethylene glycol, based on the mixture formed), homogenized and then converted into granules in an extruder with a cutting unit. The bore diameter of the multiple-bore extrusion die was 0.9 mm. The length-to-thickness ratio of the granules was 1. After rounding off and drying of the granules, the particles smaller than 0.4 mm in size and larger than 1.6 mm in size were removed by sieving. The 0.4 mm to 1.6 mm fraction was coated in a fluidized bed spray granulator of the Aeromatic STREA-1 type. The following operating parameters were established for the coating process:

| | |
|---|---|
| feed air temperature: | 47° C. |
| product temperature: | 36° C. |
| waste air temperature: | 33° C. |
| air throughput: | 90 m³/h |
| throughput rate of coating suspension: | 8 g/min |

-continued

| The coating suspension consisted of: | |
|---|---|
| titanium dioxide | 17% |
| technical stearyl alcohol | 19% |
| Eumulgin ® RT 40[a] | 3% |
| water | 61% |

[a] 40x ethoxylated castor oil, a product of Henkel KGaA.

The stearyl alcohol had the following C chain distribution: $C_{16}$ 0–5%, $C_{18}$ 95–100%, $C_{20}$ 0–2%, a hydroxyl value of 203 to 210 and a solidification range of 55° to 57.5° C.

To prepare the coating suspension, the water was heated to around 70° C. and mixed with the liquid emulsifier. The stearyl alcohol present in solid form was stirred into the water/emulsifier solution and at the same time melted. After addition of the titanium dioxide, a homogeneous emulsion in which the titanium dioxide pigment was uniformly distributed without any agglomeration was present. This coating suspension was sprayed onto the enzyme extrudate under the operating parameters mentioned above. The water of the coating suspension evaporated and was removed with the waste air. After around 285 g of coating suspension per kg of enzyme granules had been sprayed on, the extrudates were uniformly coated with a white colored and protective layer. The fatty alcohol formed a uniform non-porous film on the surface of the granules.

To determine dust abrasion, 60 g of granules were introduced into a fluidized bed. The waste air of the fluidized bed flowed through a filter. The amount of dust collected after a residence time of the enzyme granules of 40 minutes under these conditions correspond to the dust abrasion. In the present case, the dust abrasion was negligible at ≦0.04% by weight.

Example 2

The procedure was as in Example 1, except that only 150 g of the coating suspension per kg of enzyme granules were sprayed on. The final white coloring was applied in a second coating step. The precolored enzyme granules were coated with a second coating in a Glatt type GPCG-5 type rotor granulator. Instead of an aqueous coating suspension, a melt was used in the second coating stage. The coating melt had the same ingredients as the aqueous pigment suspension according to Example 1 except for the water. The stearyl alcohol was melted and was mixed while stirring with emulsifier and titanium dioxide. In this second coating stage carried out at 100° C., 8% by weight, based on the enzyme granules formed, of the melt was sprayed onto the precoated enzyme granules under the following operating conditions:

| | |
|---|---|
| feed air temperature: | 44° C. |
| product temperature: | 41° C. |
| waste air temperature: | 41° C. |
| air throughput: | 75 m³/h |
| throughput rate of coating melt: | 12 g/min |

The product coated in two stages had a higher degree of whiteness for the same quantity of titanium dioxide as in the single-stage process according to Example 1. The dust abrasion was comparably low. Like the enzyme granules of Example 1, the product has a substantially neutral odor.

Examples 3 and 4

The procedure was as described in Examples 1 and 2, except that the liquid ethoxylated castor oil in the coating melt was replaced by a solid fatty alcohol ethoxylate (Lutensol® AT 80, a product of BASF) with the following characteristic data:

| | |
|---|---|
| degree of ethoxylation: | 80 |
| cloud point: | 100° C. |
| molecular weight: | 3780 |
| dropping point: | 56° C. |
| solidification point: | 42° C. |
| viscosity at 60° C.: | 400 mPas |
| hydroxyl value: | 14 |
| HLB value: | 18.5 |

The properties of the enzyme granules thus produced did not differ significantly from those of the granules produced in accordance with Examples 1 and 2.

We claim:

1. Enzyme granules comprising enzyme, an inorganic or organic carrier material and a uniform outer pigment-containing coating layer on said granules, said outer coating layer consisting of 30 to 60% by weight of inorganic pigment, 45 to 60% by weight of an alcohol or alcohol mixture having a melting point of from 45° C. to 65° C., 5% to 15% by weight of an emulsifier for said alcohol or alcohol mixture, 0.2% to 3% by weight of a dispersant for the pigment and up to 3% by weight of water, based on the weight of said outer coating layer.

2. Enzyme granules according to claim 1 wherein said pigment is selected from the group consisting of titanium dioxide, zinc oxide, chalk, and calcium carbonate.

3. Enzyme granules according to claim 1 wherein said alcohol or alcohol mixture comprises a primary linear alcohol containing 14 to 22 carbon atoms.

4. Enzyme granules according to claim 1 wherein said emulsifier is selected from the group consisting of a primary, linear, saturated or unsaturated $C_{14-22}$ alcohol etherified with on average 25 to 50 mole equivalents of ethylene oxide, an ethoxylated fatty acid with a degree of ethoxylation of 3 to 9, an ethoxylated fatty acid amide with a degree of ethoxylation of 4 to 11, an ethoxylation product of hydroxy fatty acid esters containing 1 to 6 carbon atoms in the alcohol portion of the ester and having a degree of ethoxylation of from 5 to 80, and mixtures thereof.

5. Enzyme granules according to claim 1 having an average particle size of 0.8 mm to 1.2 mm and containing less than 2% by weight of particles with sizes smaller than 0.4 mm and larger than 1.6 mm.

6. Enzyme granules according to claim 1 wherein said enzyme is selected from the group consisting of protease, amylase, lipase and cellulase.

7. Enzyme granules according to claim 1 wherein said enzyme comprises protease having an activity of 150,000 PU to 350,000 PU per gram of enzyme granules.

8. The process of producing enzyme granules comprising extruding an enzyme compound formed by mixing a concentrated enzyme fermentation broth with inorganic or organic carrier material, optionally spheronizing the extrudate in a spheronizer, drying the extrudate, and applying an outer coating layer to the extrudate wherein said outer coating layer consists of 30% by weight to 50% by weight of inorganic pigment, 45% by weight to 60% by weight of an alcohol or alcohol mixture having a melting point of 45° C. to 65° C., 5% to 15% by weight of an emulsifier for said alcohol or alcohol mixture, 0.2% to 3% by weight of a dispersant for the pigment and up to 3% by weight of water, based on the weight of said outer coating layer.

9. A process according to claim 8 wherein said step of applying said outer coating layer to said extrudate is conducted in a fluidized bed drying apparatus.

10. A process according to claim 8 wherein from 6% to 15% by weight, based on said enzyme granules, of said coating layer is applied to said extrudate.

11. A process according to claim 8 wherein said coating layer is applied to said extrudate as an aqueous dispersion and the water is removed therefrom by drying at a temperature which heats said enzyme granules to a temperature of not more than 42° C.

12. A process according to claim 11 wherein said dispersion contains 50% to 70% by weight of water and 30% to 50% by weight of the coating composition wherein the coating composition contains 1% to 2.5% by weight, based on the coating composition, of a dispersant for said pigment.

13. A process according to claim 8 wherein said outer coating layer is applied to said extrudate as a liquid which is present at a temperature of 5° C. to 45° C. above the melting point of said alcohol.

14. A process according to claim 8 including spheronizing the extrudate and drying the extrudate to a water content of 4% to 10% by weight at a temperature of from 35° C. to 50° C.

15. A particulate detergent composition containing the enzyme granules of claim 1.

* * * * *